(12) United States Patent
Lehel et al.

(10) Patent No.: US 7,907,766 B2
(45) Date of Patent: Mar. 15, 2011

(54) AUTOMATIC CORONARY ARTERY CALCIUM DETECTION AND LABELING SYSTEM

(75) Inventors: Peter Lehel, Oconomowoc, WI (US);
Saad A Sirohey, Pewaukee, WI (US);
DeAnn M Haas, Port Washington, WI (US); Pradipto Kolay, Bangalore (IN)

(73) Assignee: General Electric Company, Schenectady, NY (US)

( * ) Notice: Subject to any disclaimer, the term of this patent is extended or adjusted under 35 U.S.C. 154(b) by 1108 days.

(21) Appl. No.: 11/619,182

(22) Filed: Jan. 2, 2007

(65) Prior Publication Data

US 2008/0159610 A1  Jul. 3, 2008

(51) Int. Cl.
*G06K 9/00* (2006.01)
*A61B 6/00* (2006.01)
*G06F 19/00* (2011.01)

(52) U.S. Cl. ............... 382/131; 378/4; 600/481; 702/19
(58) Field of Classification Search .................. 382/131; 378/4; 600/481; 702/19
See application file for complete search history.

(56) References Cited

U.S. PATENT DOCUMENTS 6,990,222 B2 * 1/2006 Arnold ........................... 382/131
7,558,611 B2 * 7/2009 Arnold et al. ................. 600/407
2004/0133100 A1 * 7/2004 Naghavi et al. ............... 600/425
2008/0273652 A1 * 11/2008 Arnold et al. ...................... 378/4
2008/0279435 A1 * 11/2008 Arnold et al. ................. 382/131

OTHER PUBLICATIONS

Isgum et al. "Automated Coronary Calcification Detection and Scoring," Proceedings of the 4th International Symposium on Image and Signal Processing and Analysis, Sep. 15-17, 2005, pp. 127-132.*
W.J. Niessen, C.M. Van Bemmel, A.E. Frangi, M.J.A. Siers. O. Wink, Model-based segmentation of cardiac and vascular images, Biomedical Imaging, 2002. Proceedings. 2002 IEEE International Symposium, 2002, pp. 22-25.
Rumberger, A rosetta stone for coronary calcium risk stratification, AJR Am. J., 2003, 181:743-748.
Agatston, Arthur S. et al; "Quantification of Coronary Artery Calcium Using Ultrafast Computed Tomography"; JACC v. 15 No. 4, Mar. 15, 1990: 827-832.

* cited by examiner

*Primary Examiner* — Bhavesh M Mehta
*Assistant Examiner* — Stephen R Koziol
(74) *Attorney, Agent, or Firm* — Dean Small; The Small Patent Law Group

(57) ABSTRACT

Method and system for using segmentation and three-dimensional image-processing techniques of a method to create an automatic method to detect coronary artery calcification deposits and identify their location with respect to a major coronary artery. Finally, different scoring algorithms can be applied to generate calcium scores such as Agatston Janovitz, Mass, and Volume. A total score and a more detailed score can be generated based on the major arteries such as right coronary artery, left anterior descending artery, or left circumflex artery to be incorporated into the patient report.

22 Claims, 9 Drawing Sheets

US 7,907,766 B2

AUTOMATIC CORONARY ARTERY CALCIUM DETECTION AND LABELING SYSTEM

FIELD OF THE INVENTION

This invention relates generally to an automated method for detecting coronary artery calcification, and more particularly to measurements of calcium, volume, and mass in the vascular system of a living body.

BACKGROUND OF THE INVENTION

Coronary artery disease (CAD) is a leading cause of death in the developed world. The reference diagnostic imaging exam for the diagnosis of CAD is coronary angiography that enables the detection of blockages or obstructions in the coronary arteries through the buildup of plaque. Coronary angiography is an invasive exam that would be prohibitive to apply to a large asymptomatic population for the purpose of earlier detection of the disease.

Coronary artery calcification (CAC) or coronary artery calcium scoring (CACS) is a good indicator of the presence of plaque and can be imaged using non-invasive methods like computed tomography (CT). Cardiac CT is particularly useful in assisting medical providers in assessing the risk of cardiovascular disease that can lead to heart failure or a stroke. One particular implementation of cardiac CT is the detection of calcium deposits in the coronary arteries of medical patients. These deposits have to be reviewed by a physician and labeled according to the artery location and a total score is reported using the most common algorithm. Such manual procedures are labor intensive and time consuming, as well as being prone to error in exact positioning. Further, many objects in the image, such as calcified plaque, have an irregular margin such that a fixed geometry will be over inclusive by containing non-calcified tissue or will be under inclusive by omitting a portion of the calcified plaque.

For the reasons stated above, and for other reasons stated below which will become apparent to those skilled in the art upon reading and understanding the present specification, there is a need in the art for accurate detection and labeling of coronary artery calcification using an automated method. There is also a need for improved segmentation technique, three dimensional (3D) image processing, and region labels that in combination generate calcium score automatically.

BRIEF DESCRIPTION OF THE INVENTION

The above-mentioned shortcomings, disadvantages and problems are addressed herein, which will be understood by reading and studying the following specification.

In one aspect, an automated method for detecting coronary artery calcification performing the action of creating a three dimensional (3D) bounding volume by analyzing a set of images, wherein the bounding volume includes a heart; applying a reticle on the created bounding volume so as to divide the bounding volume into regions; analyzing each region to identify calcified plaques that exceed a predetermined value; and generating quantitative measurements for the identified calcified plaques that exceed a predetermined value.

In another aspect, the quantitative measurements are one of calcium score, volume, mass.

In yet another aspect, the set of images are produced by one or more computed tomography (CT) system, magnetic resonance imaging (MRI) system, positron emission tomography (PET) system, photon emission computed tomography (SPECT) system.

In still another aspect, the bounding volume includes segmenting the heart from the set of images by applying one or more model based segmentation approach, and lung segmentation and localization of the heart.

In a further aspect, the analyzing each region to identify calcified plaques further comprises performing one or more thresholding, morphology, labeling, and centroid analysis.

In another aspect, proving a user interface (UI) for user initiated modification of the bounding volume, or identification of calcified plaques; and the reticle creates at least one or more right coronary artery (RCA) region, left anterior descending artery (LAD) region, or left circumflex artery (LCX) region.

In a further aspect, generating quantitative measurements comprises selecting one or more Agatston Janovitz (AJ) algorithm, volume algorithm, mass algorithm, or user-defined algorithm for calculating quantitative measurements; generating a report showing the quantitative measurements for each region of the bounding volume as performed by the selected one or more algorithms for calculating quantitative measurements.

In yet a further aspect, a computer-accessible medium to detect coronary artery calcification for directing a processor to perform creating a three dimensional (3D) bounding volume by analyzing a set of images, wherein the bounding volume includes a heart; applying a reticle on the created bounding volume so as to divide the bounding volume into regions; analyzing each region to identify calcified plaques that exceed a predetermined value; and generating quantitative measurements for the identified calcified plaques that exceed a predetermined value.

In still yet a further aspect, the processor performing receiving user initiated modification of the bounding volume, or identification of calcified plaques and generating a report showing the quantitative measurements for each region of the bounding volume as performed by the selected one or more algorithms for calculating quantitative measurements.

In yet a further aspect, a system for detecting coronary artery calcification comprising a processor; a storage device coupled to the processor; and, software means operative on the processor for: creating a three dimensional (3D) bounding volume by analyzing a set of images, wherein the bounding volume includes a heart; applying a reticle on the created bounding volume so as to divide the bounding volume into regions; analyzing each region to identify calcified plaques that exceed a predetermined value; and generating quantitative measurements for the identified calcified plaques that exceed a predetermined value; wherein the reticle creates at least one or more right coronary artery (RCA) region, left anterior descending artery (LAD) region, or left circumflex artery (LCX) region; wherein the set of images are one or more image using at least a computed tomography (CT) system, magnetic resonance imaging (MRI) system, positron emission tomography (PET) system, photon emission computed tomography (SPECT) system; wherein creating a bounding volume is segmenting the heart from the set of images by applying one or more model based segmentation approach, and lung segmentation and localization of the heart; wherein analyzing each region to identify calcified plaques is performing one or more thresholding, morphology, labeling, and centroid analysis; wherein the quantitative measurements are one of calcium score, volume, mass.

In still yet a further aspect, a user interface (UI) for making user initiated modification of the bounding volume, or identification of calcified plaques; selecting one or more Agatston Janovitz (AJ) algorithm, volume algorithm, mass algorithm, or user defined algorithm for calculating quantitative measurements; generating a report showing the quantitative measurements for each region of the bounding volume as performed by the selected one or more algorithms for calculating quantitative measurements.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
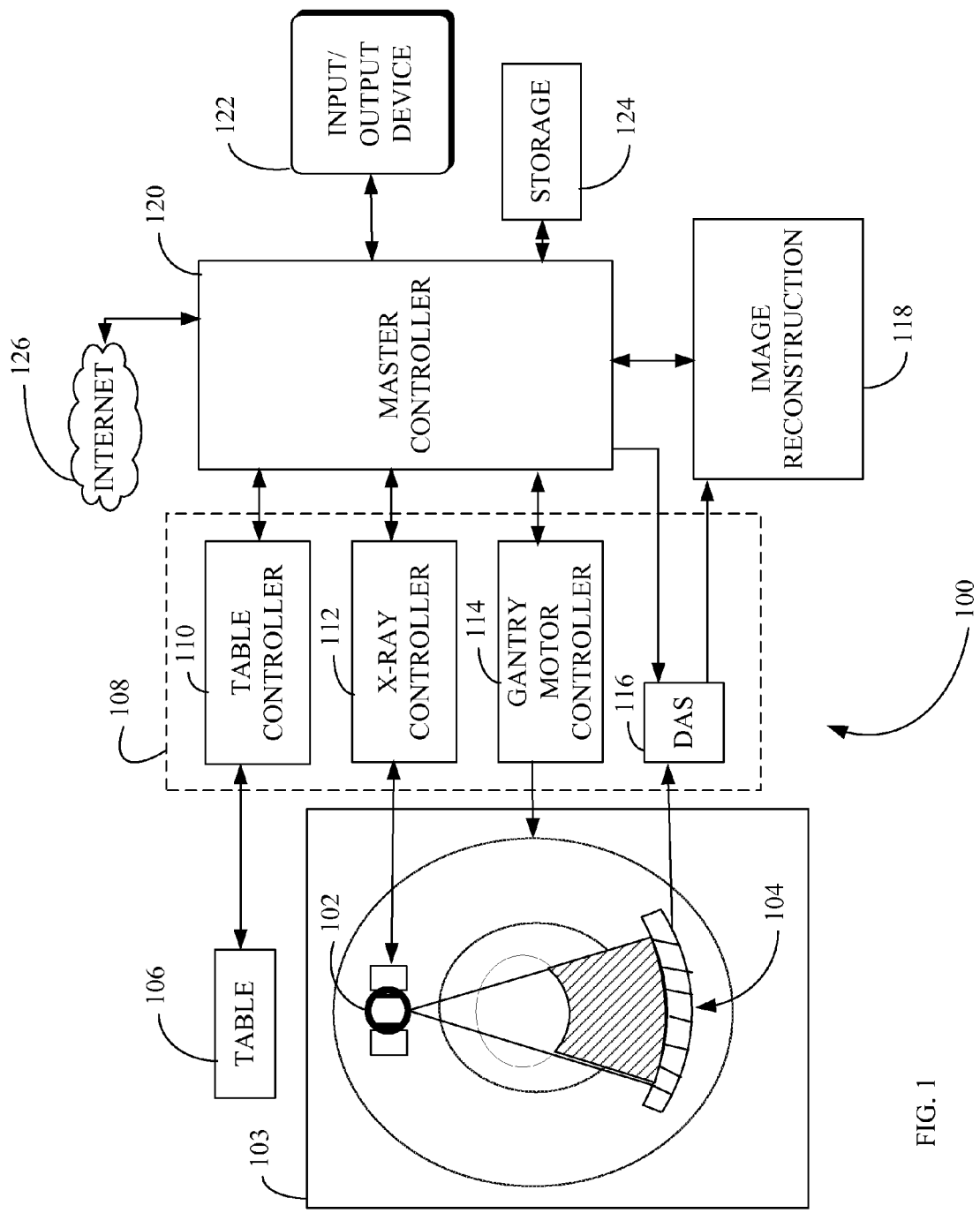
FIG. 1 is a diagram illustrating a system-level overview of an embodiment.

FIG. 1 is a block diagram of an overview of a system to perform automatic detection coronary artery calcification. CT imaging system 100 solves the need in the art for accurate detection and labeling of coronary artery calcification using an automated method. CT imaging system 100 includes a gantry 103, table 106, controllers 108, master controller, and image reconstruction device 118. It should be noted that other data acquisition systems are envisioned including a magnetic resonance (MRI) imaging system, a positron emission tomography (PET) system, a single photon emission computed tomography (SPECT) system, an ultrasound system, or an X-ray system. The data acquisition system obtains data including, but not limited to image data, functional image data, and temporal image data. Further examples of data include voxel data including volume information for a three dimensional region of interest (ROI), pixel data including area information for a two dimensional region of interest, and spatio-temporal data. Spatio-temporal data includes area or volume information over a selected, predetermined time period.

CT imaging system 100 includes a gantry 103 having an X-ray source 102, a radiation detector array 104, a patient support structure and a patient cavity, wherein the X-ray source 102 and the radiation detector array 104 are diametrically disposed so as to be separated by the patient cavity. In an exemplary embodiment, a patient (not shown) is disposed upon the patient support structure, which is then disposed within the patient cavity. The X-ray source 102 projects an X-ray beam toward the radiation detector array 104 so as to pass through the patient. In an exemplary embodiment, the X-ray beam is collimated by a collimate (not shown) so as to lie within an X-Y plane of a Cartesian coordinate system referred known to those in the art as the imaging plane. After passing through and becoming attenuated by the patient, the attenuated X-ray beam is received by the radiation detector array 104. In preferred embodiment, the radiation detector array 104 includes a plurality of detector elements wherein each of said detector elements receives an attenuated X-ray beam and produces an electrical signal responsive to the intensity of the attenuated X-ray beam.

In addition, the X-ray source 102 and the radiation detector array 104 can rotate relative to the gantry 103 and the patient support structure, so as to allow the X-ray source 102 and the radiation detector array 104 to rotate around the patient support structure when the patient support structure is disposed within the patient cavity. X-ray projection data is obtained by rotating the X-ray source 102 and the radiation detector array 104 around the patient during a scan. The X-ray source 102 and the radiation detector array 104 communicate with a control mechanism 108 associated with the CT imaging system 100. The control mechanism 108 controls the rotation and operation of the X-ray source 102 and the radiation detector array 104.

The table controller 110, X-ray controller, gantry motor controller, DAS 116, image reconstruction 118, and master controller 120 have the same hardware and capabilities that is only limited by the programming in each respective device. For the purpose of the description, all controllers are presumed to have the same hardware so a discussion to one applies to all. The master controller 120 provides computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

The master controller 120 includes a processor, commercially available from Intel, Motorola, Cyrix and others. Master controller 120 also includes random-access memory (RAM), read-only memory (ROM), and one or more mass storage devices 124, and a system bus that operatively couples various system components to the processing unit of master controller 120. The memory and mass storage devices are types of computer-accessible media. Mass storage devices are more specifically types of nonvolatile computer-accessible media and can include one or more hard disk drives, floppy disk drives, optical disk drives, and tape cartridge drives. The computer readable medium can be an electronic, a magnetic, an optical, an electromagnetic, or an infrared system, apparatus, or device. An illustrative, but non-exhaustive list of computer-readable mediums can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical). Note that the computer readable medium may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory. The processor in the master controller executes computer programs stored on the computer-accessible media.

Master controller 120 can be communicatively connected to the Internet 126 via a communication device. Internet 126 connectivity is well known within the art. In one embodiment, a communication device is a modem that responds to communication drivers to connect to the Internet via what is known in the art as a "dial-up connection." In another embodiment, a communication device is an Ethernet® or similar hardware network card connected to a local-area network (LAN) that itself is connected to the Internet via what is known in the art as a "direct connection" (e.g., T1 line, etc.).

A user enters commands and information into the master controller 120 through input device 122 such as a keyboard or a pointing device. The keyboard permits entry of textual information into master controller 120, as known within the art, and embodiments are not limited to any particular type of keyboard. Pointing device permits the control of the screen pointer provided by a graphical user interface (GUI) of operating systems such as versions of Microsoft Windows®. Embodiments are not limited to any particular pointing device. Such pointing devices include mice, touch pads, trackballs, remote controls and point sticks. Other input devices (not shown) can include a microphone, joystick, game pad, satellite dish, scanner, or the like. For the purpose of this description, a keyboard and a pointing device are referred to as a user interface (UI) that allows the user to interact with the automated calcium detection system, algorithm, or structure. The output device is a display device. Display device is connected to the system bus. Display device permits the display of information, including computer, video and other information, for viewing by a user of the computer. Embodiments are not limited to any particular display device. Such display devices include cathode ray tube (CRT) displays (monitors), as well as flat panel displays such as liquid crystal displays (LCD's). In addition to a monitor, computers typically include other peripheral input/output devices such as printers (not shown). The controllers also include an operating system (not shown) that is stored on the computer-accessible media RAM, ROM, and mass storage device 124, and is and executed by the processor in the controller. Examples of operating systems include Microsoft Windows®, Apple MacOS®, Linux®, UNIX®. Examples are not limited to any particular operating system, however, and the construction and use of such operating systems are well known within the art.

Master controller 120 can be operated using at least one operating system to provide a graphical user interface (GUI) including a user-controllable pointer. Master controller can have at least one web browser application program executing within at least one operating system, to permit users of the controller to access intranet or Internet world-wide-web pages as addressed by Universal Resource Locator (URL) addresses. Examples of browser application programs include Netscape Navigator® and Microsoft Internet Explorer.

In an exemplary embodiment, the control mechanism 108 includes an X-ray controller 112 communicating with an X-ray source 102, a gantry motor controller 114, and a data acquisition system (DAS) 116 communicating with a radiation detector array 104. The X-ray controller 112 provides power and timing signals to the X-ray source 102, the gantry motor controller 114 controls the rotational speed and angular position of the X-ray source 102, and the radiation detector array 104 and the DAS 116 receive the electrical signal data produced by detector elements 104 and convert this data into digital signals for subsequent processing. In an exemplary embodiment, the CT imaging system 100 also includes an image reconstruction device 118, a data storage device 124 and a master controller 120, wherein the processing device 120 communicates with the image reconstruction device 118, the gantry motor controller 114, the X-ray controller 112, the data storage device 124, an input and an output device 122. The CT imaging system 100 can also include a table controller 110 in communication with the master controller 120 and the patient support structure, so as to control the position of the patient support structure relative to the patient cavity.

In accordance with the preferred embodiment, the patient is disposed on the patient support structure, which is then positioned by an operator via the master controller 120 so as to be disposed within the patient cavity. The gantry motor controller 114 is operated via master controller 120 so as to cause the X-ray source 4 and the radiation detector array 6 to rotate relative to the patient. The X-ray controller 112 is operated via the master controller 120 so as to cause the X-ray source 102 to emit and project a collimated X-ray beam toward the radiation detector array 104 and hence toward the patient. The X-ray beam passes through the patient so as to create an attenuated X-ray beam, which is received by the radiation detector array 104.

The detector elements 104 receive the attenuated X-ray beam, produce electrical signal data responsive to the intensity of the attenuated X-ray beam and communicate this electrical signal data to the DAS 116. The DAS 116 then converts this electrical signal data to digital signals and communicates both the digital signals and the electrical signal data to the image reconstruction device 118, which performs high-speed image reconstruction. This information is then communicated to the master controller 120, which stores the image in the data storage device 124 and displays the digital signal as an image via output device 122. The information communicated to the master controller 120 is referred to as ROI image data. In accordance with an exemplary embodiment, the output device 122 includes a display screen having a plurality of discrete pixel elements.

In the previous paragraphs, a system level overview of the operation of an embodiment is described. In this section, the particular methods of such an embodiment are described by reference to a series of flowcharts. Describing the methods by reference to a flowchart enables one skilled in the art to develop such programs, firmware, or hardware, including such instructions to carry out the methods on suitable computers, executing the instructions from computer-readable media. Similarly, the methods performed by the server computer programs, firmware, or hardware are also composed of computer-executable instructions. The methods are performed by a program executing on, or performed by firmware or hardware that is a part of, a computer, such as master controller 120 in FIG. 1.

Figure 2:
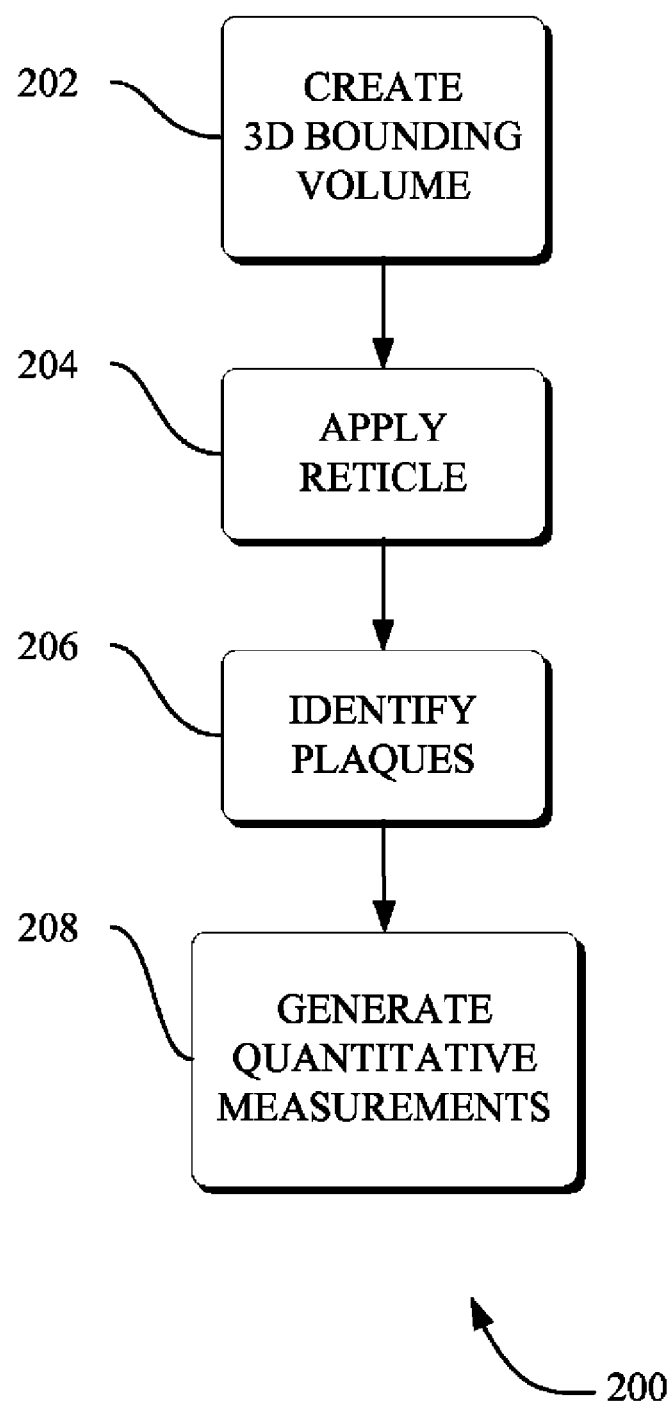
FIG. 2 is a flowchart of a method performed by a client according to an embodiment.

FIG. 2 is a flowchart of a method 200 performed by a client according to an embodiment. Method 200 solves the need in the art for accurate detection and labeling of coronary artery calcification using an automated method.

Method 200 includes creation of a three dimensional (3D) bounding volume 202, application of a reticle 204, identification of plaques 206, and the generation of quantitative measurements 208 that describe the identified plaques.

Method 200 begins 202 that creates a three dimensional (3D) bounding volume. The basic idea is to input a stack of CT axial slices and produce as an output a 3D bounding volume that includes the heart. Each axial CT image comprises a plurality of voxels wherein the intensity of each voxel is representative of an X-ray attenuation value of a corresponding location within the heart region. The voxels within the images that contain calcifications are referred to as fragments. While the invention is described with reference to a computed tomography (CT) system, it should be understood that the method, system and computer product of the present invention may be applied to other data acquisition systems, such as a magnetic resonance imaging system (MRI), a positron emission tomography system (PET), a single photon emission computed tomography system (SPECT), an ultrasound system, or a X-ray system. The first step in producing a 3D bounding volume is to segment the heart.

Heart segmentation is a challenge in non-contrast computed tomography (CT) studies such as CAC screening. There are two possible segmentation approaches the model based approach and the lung segmentation and localization of the heart. An example of the model based approach is when landmarks of an atlas are propagated to all other shapes of the atlas using a quasi-affine registration and an elastic registration. See W. J. Niessen, C. M. van Bemmel, A. F. Frangi, M. J. A. Siers, and O. Wink, "Model-based segmentation of cardiac and vascular images," in Proceedings of the IEEE International Symposium on Biomedical Imaging (ISBI), 2002, pp. 22-25. The Niessen et al publication is hereby incorporated by reference in its entirety. Method 300 (FIG. 3) addresses model base segmentation. In the lung segmentation and localization of the heart, local features through attenuation levels are used to pinpoint features that can indicate the lungs or recognizable blood vessels and by noting that the heart is positioned within a surrounding region of fat tissue and lung tissue. Method 900 (FIG. 9) addresses lung segmentation and localization of the heart. The operator may augment or modify the 3D bounding volume through a keyboard, a light pen, or a mouse. Once action 202 determines the 3D bounding volume control passes to action 204 for further processing.

Figure 6:
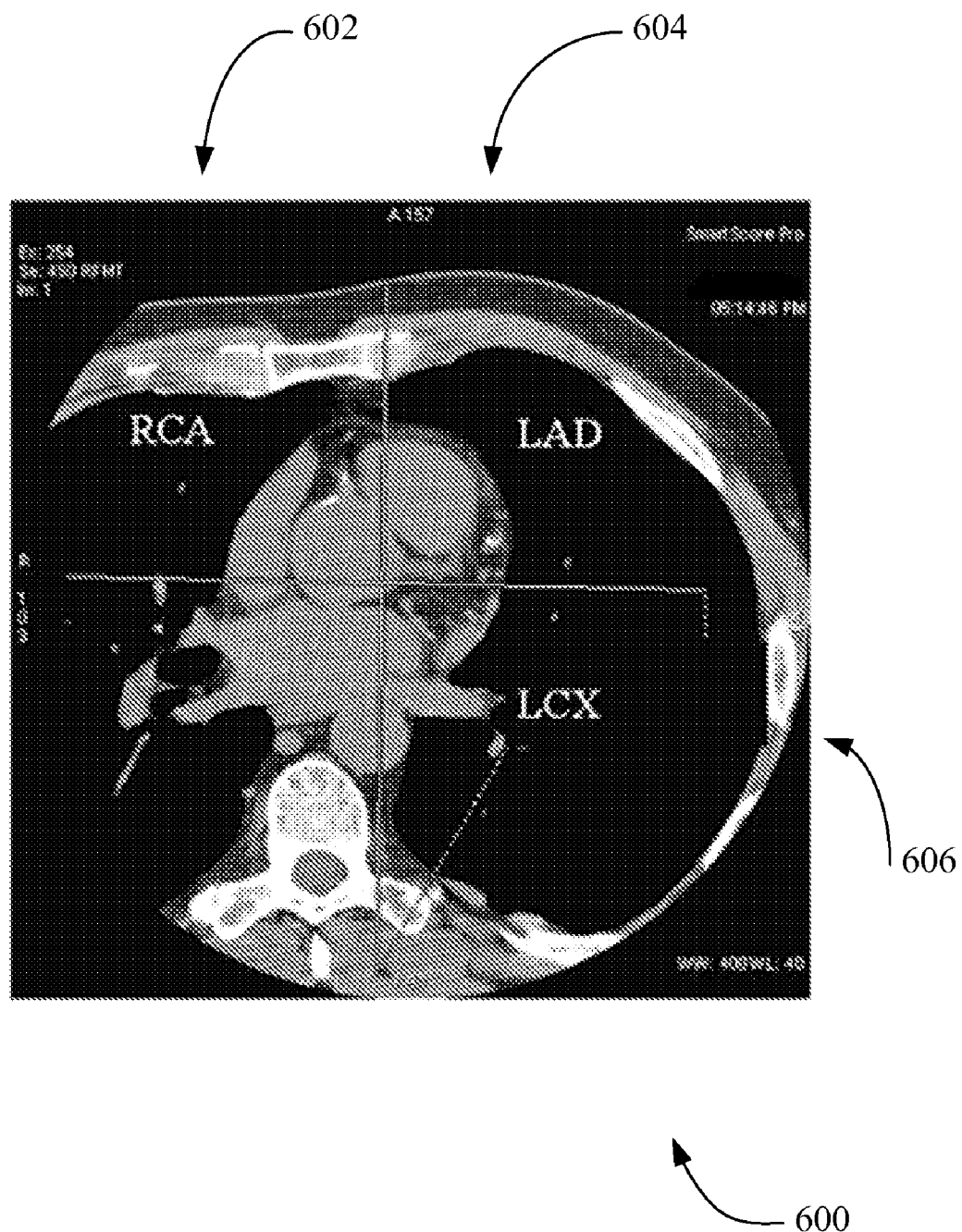
FIG. 6 is a display of an axial viewport showing an example of a reticle on three dimensional (3D) bounding volume.

In action 204, a reticle is applied to the 3D bounding volume including the heart. The skilled artisan will appreciate that, in the context of such alternative applications, a reticle, reticule, graticule is a network of fine lines, dots, crosshairs, or wires in the 3D bounding volume or on the display that permits the creation of regions for determining position. In the preferred embodiment an artery crosshair tool is automatically displayed over the axial viewport allowing the labeling of the major arteries such as right coronary artery (RCA) region 602, left anterior descending artery (LAD) region 604, or left circumflex artery (LCX) region 606 all in FIG. 6. This tool can be positioned, rotated, and modified to fit any patient's heart. As shown in FIG. 6 one or more regions of the axial viewport can be described with reference to a crosshair label. The operator can reposition the reticle by using an aptly programmed user interface (UI) as described in FIG. 8. After applying a reticle in action 204 control passes to action 206 for further processing.

In action 206 plaques are identified. In action 206 the method looks at each reticle created region and identifies fragments that are above predetermined threshold value. The operation of identifying a calcified object within a reticle created region is performed by the computer system in hardware, in software, or in both hardware and software. The method also accepts operator modification to correct for spurious results. The detection component consists of a threshold-based identification of all calcified areas within the heart region of interest (ROI) and morphological operators and segment each calcified plaque. Labeling is then applied to each connected plaque component based on its location with respect to the artery crosshair tool. The algorithm also stores the center of gravity of each plaque. Once the plaques have been identified control passes to action 208 for further processing.

In action 208, quantitative measurements are generated for fragments within the region of interest (ROI). The quantitative measurement 208 is the application of scoring algorithms to generate calcium scores such as Agatston Janovitz (AJ), Mass and Volume. A total score and a more detailed score can be generated based on the major arteries RCA, LAD and LCX to be incorporated into the patient report.

Figure 3:
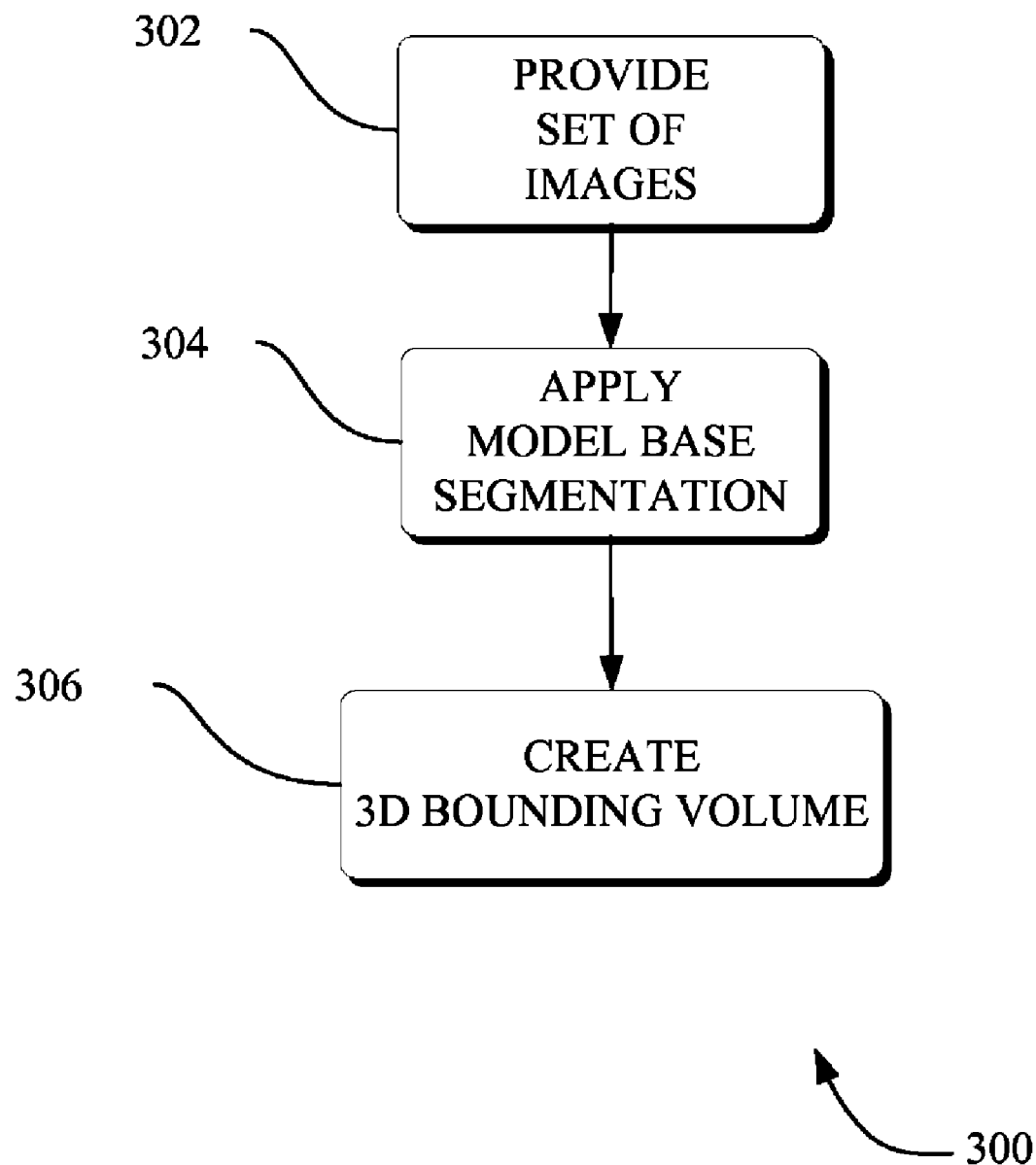
FIG. 3 is a flowchart of a method performed by a client according to an embodiment for creating three dimensional (3D) bounding volume using model base segmentation.

FIG. 3 is a flowchart of a method 300 performed by a client according to an embodiment. Method 300 solves the need in the art for accurate detection and labeling of coronary artery calcification using an automated method.

Method 300 creates a three dimensional (3D) bounding volume 306 from image data 302 that underwent model base segmentation 304.

Method 300 begins with action 302. In action 302 a set of images is received from a medical imaging system 100 such as a computed tomography (CT) system, from a storage device 124, or from an external device connected to the medical imaging system 100 through the internet 126. The set of images is a stack of CT axial slices of cross-sectional views of the patient's heart region. Calcium has a higher density or X-ray attenuation value than normal body tissue, so the axial CT images provide contrast between calcification and surrounding tissue. Once the set of images have been received control passes to action 304 for further processing.

In action 304, model based segmentation is applied to the stack of CT axial slices. In model based segmentation the stack of CT axial slices is represented by triangular mashes, superquadrics, and other complex shapes. Once the model based segmentation has been performed control passes to action 306 for further processing.

In an action 306 a 3D bound volume is created. The bounding volume for the region of the heart is a closed volume that completely contains the region of interest (ROI) such as the heart and major arteries. A common type of bounding volume is a bounding box or a cuboid, or in 2-D a rectangle, containing the region of interest.

Figure 9:
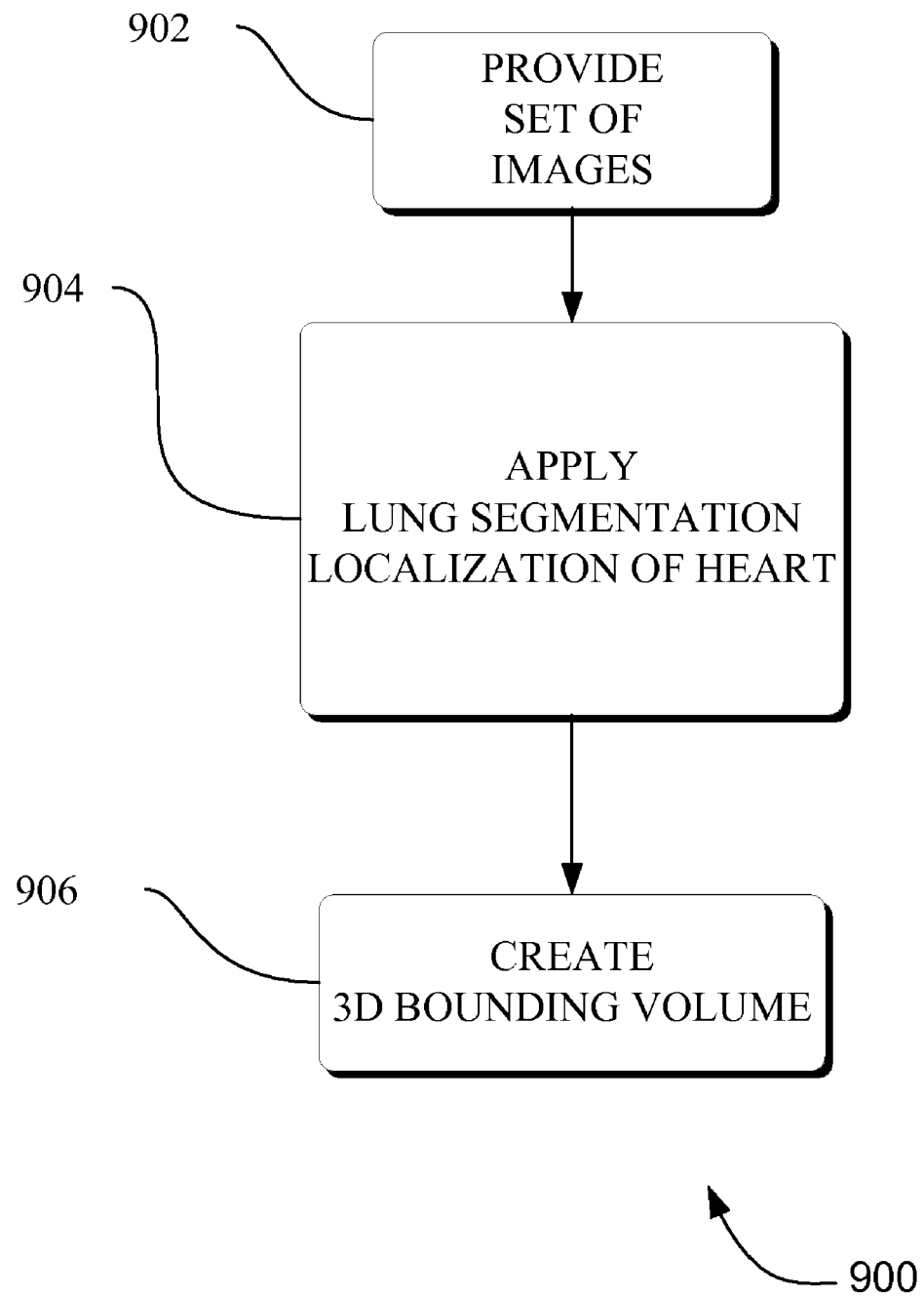
FIG. 9 is a flowchart of a method performed by a client according to an embodiment for creating three dimensional (3D) bounding volume using lung segmentation and localization of the heart.

FIG. 9 is a flowchart of a method 900 performed by a client according to an embodiment. Method 900 solves the need in the art for accurate detection and labeling of coronary artery calcification using an automated method.

Method 900 creates a three dimensional (3D) bounding volume 906 from image data 902 that underwent lung segmentation and localization of the heart 906.

Method 900 begins with action 902. In action 902 a set of images is received from a medical imaging system 100 such as a computed tomography (CT) system, from a storage device 124, or from an external device connected to the medical imaging system 100 through the internet 126. The set of images is a stack of CT axial slices of cross-sectional views of the patient's heart region. Calcium has a higher density or X-ray attenuation value than normal body tissue, so the axial CT images provide contrast between calcification and surrounding tissue. Once the set of images have been received control passes to action 904 for further processing.

In action 904 a segmentation performed by localizing the heart. In particular in lung segmentation and localization of the heart, local features through attenuation levels are used to pinpoint features that can indicate the lungs or recognizable blood vessels and by noting that the heart is positioned within a surrounding region of fat tissue and lung tissue.

In an action 906 a 3D bound volume is created. The bounding volume for the region of the heart is a closed volume that completely contains the region of interest (ROI) such as the heart and major arteries. A common type of bounding volume is a bounding box or a cuboid, or in 2-D a rectangle, containing the region of interest.

Figure 4:
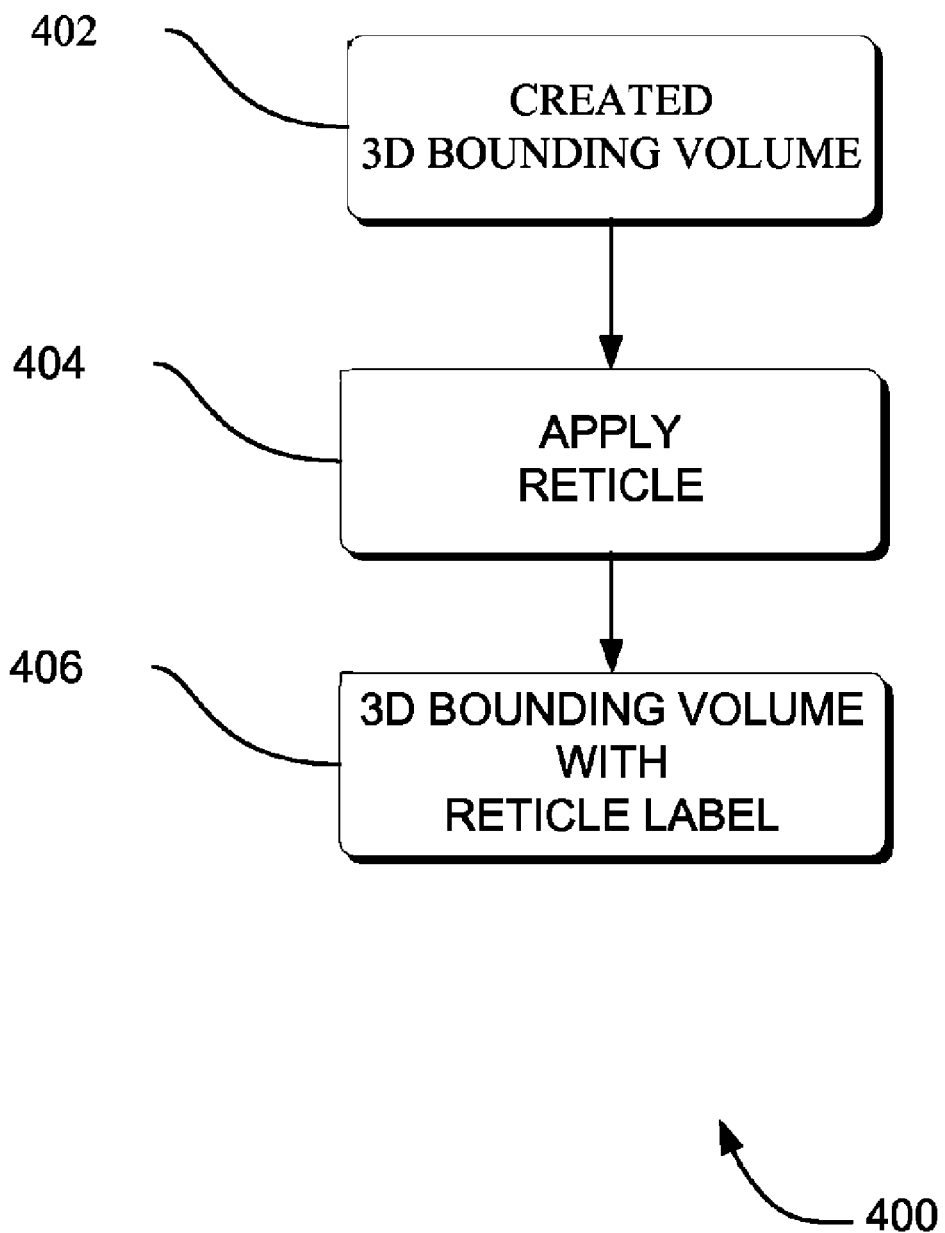
FIG. 4 is a flowchart of a method performed by a client according to an embodiment for applying a reticle to a three dimensional (3D) bounding volume.

FIG. 4 is a flowchart of a method 400 performed by a client according to an embodiment. Method 400 solves the need in the art for accurate detection and labeling of coronary artery calcification using an automated method.

Method 400 creates a three dimensional (3D) bounding volume 406 with an applied reticle from a 3D bounding volume 402 and a reticle 404.

Method 400 begins with action 402. In action 402 a 3D bounding volume from the CT images is created or received from storage if the 3D bounding volume was previously created. Once action 402 is performed control passes to action 404 for further processing.

In action 404 a reticle is applied to the 3D bounding volume. An artery crosshair tool is automatically displayed over the axial viewport allowing the labeling of the major arteries such as RCA, LAD and LCX. This tool can be positioned, rotated and modified to fit any patient's heart as described in FIG. 8. In most cases, the three major arteries shall stay in their assigned quadrants.

In action 406, the 3D bounding volume is displayed with the reticle label. In FIG. 6 a crosshair tool for labeling the major arteries (RCA, LAD, and LCX) as seen by the user of the medical imaging system 100.

Figure 5:
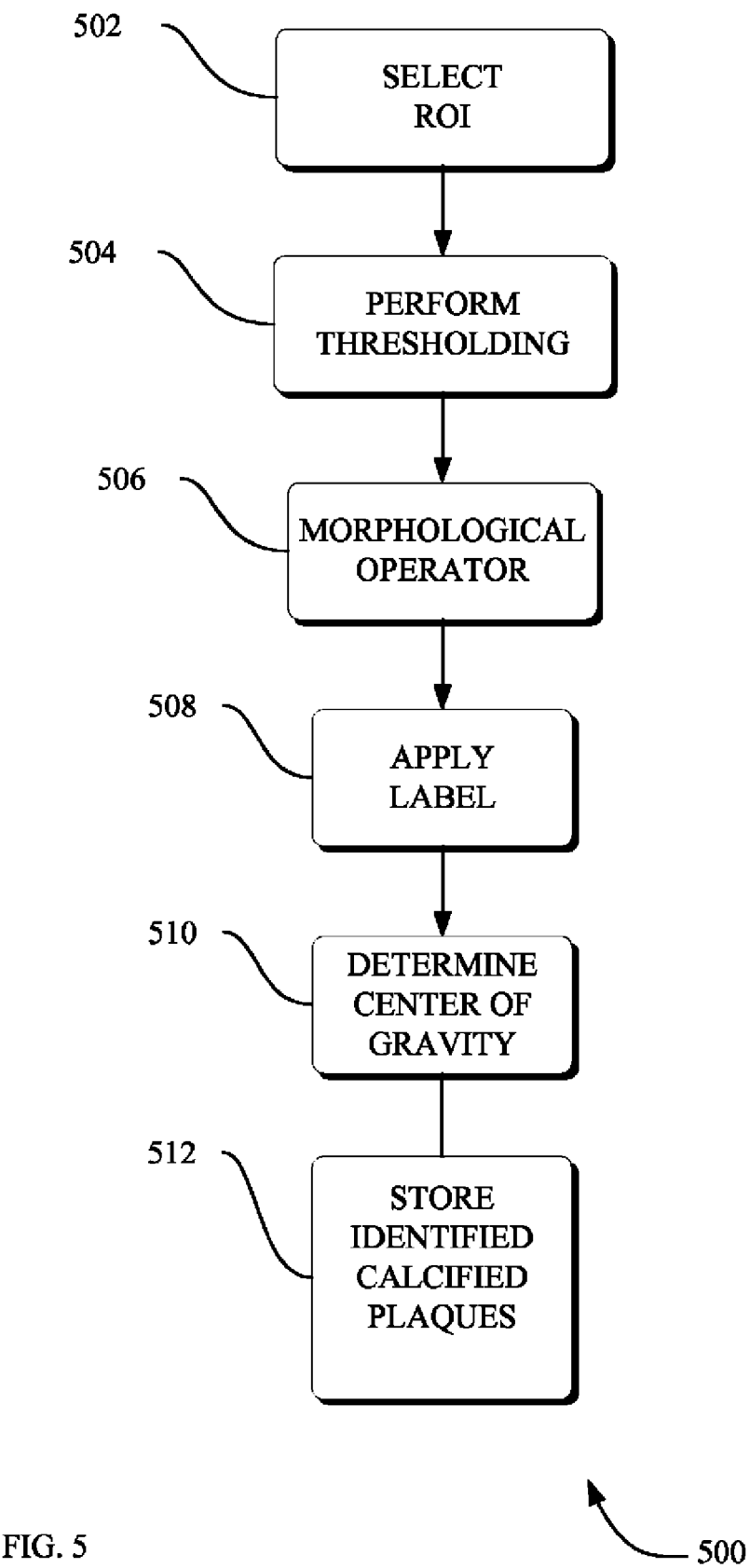
FIG. 5 is a flowchart of a method performed by a client according to an embodiment for identifying calcified plaques.

FIG. 5 is a flowchart of a method 500 performed by a client according to an embodiment. Method 500 solves the need in the art for accurate detection and labeling of coronary artery calcification using an automated method.

Method 500 takes a region of interest (ROI) 502 which consists of the 3D bounding volume and the localized labeling tool (reticle), performs thresholding 504, morphological operations 506, labeling 508, determination of center of gravity 510, and storing of identified calcified plaques 512.

Method 500 begins with action 502. A ROI consisting of the 3D bounding volume and the localized labeling tool is selected. The selection can be all quadrants identified by the reticle or a specific quadrant of the reticle. Once the ROI has been selected 502 control passes to action 504 for further processing.

In action 504 thresholding is performed on the selected region of interest. Applying a threshold typically facilitates identification of all pixels above the threshold as containing calcium. A threshold selected from the range of 80 to 140 Hounsfield units (HU) is applied to the CT image. It is customary to select a threshold value of 130 HU for thresholding. Once thresholding has been applied control passes to action 506 for further processing. In X-ray attenuation the voxels having X-ray attenuation values greater than or equal to a predetermined threshold value are identified. The predetermined threshold value is dependent on the X-ray detector 104 and the characteristics of the subject being scanned. For example, a predetermined value for a small person may not be adequate for a larger person. The predetermined X-ray attenuation ranging from 80 HU to 140 HU should be able to accommodate differences in the anatomy and differences in the equipment being used. Also the predetermined value can be selected from image statistics such as mean and standard deviation of the X-ray attenuation value in the CT image of the heart region. For example, the predetermined value can be based on the mean or values that are within standard deviations from the mean value. Calibration can be used to minimize the variations in attenuation due to the X-ray system and the physiology of the patient.

In action 506 morphological operations are performed. The thresholding occasionally includes extraneous information that needs to be removed. Morphological operators such as Dilation (grow image regions), Erosion (shrink image regions), Opening (structured removal of image region boundary pixels), Closing (structured filling in of image region boundary pixels), Hit and Miss Transform (image pattern matching and marking), Thinning (structured erosion using image pattern matching), Thickening (structured dilation using image pattern matching), Skeletonization/Medial Axis Transform (finding skeletons of binary regions) can be used to remove the extraneous information. Once the morphological operators have been performed control passes to action 508 for further processing.

In action 508, a label is applied to identify calcified plaques with respect to the artery crosshair tool 600. The labeling allows the automated method to pinpoint the location of the plaque relative to the crosshair tool 600. Once the plaques have been identified and labeled control passes to action 510 for further processing.

In action 510, a center of gravity is determined. The center of gravity is determined by computing the centroid or center of gravity of groups of contiguous pixels found by the thresholding process 504. Once the center of gravity is determined control passes to action 512 for further processing.

In action 512, the identified calcified plaques are store for later retrieval. The identified calcified plaques information is stored in a storage medium at block 124. The storage medium includes, but is not limited to, for example, a remote server, a DICOM object, or any computer based storage medium. The identified calcified plaques information is stored for either a short or a long period of time at a user's discretion. In an exemplary embodiment, identified calcified plaques information including ROI pixel data, a label of the ROI artery type, and a result of a calculation of a coronary artery calcium score, mass, or volume value of the ROI is stored.

FIG. 6 is a representation of a display of the reticle on the 3D bounding volume. Display 600 solves the need in the art for accurate detection and labeling of coronary artery calcification using an automated method. Display 600 is a crosshair tool that shows the 3D bounding volume having regions that can be labeled with the major artery. The display 600 is labeled with the major arteries such as right coronary artery (RCA) region 602, left anterior descending artery (LAD) region 604, or left circumflex artery (LCX) region 606.

Figure 7:
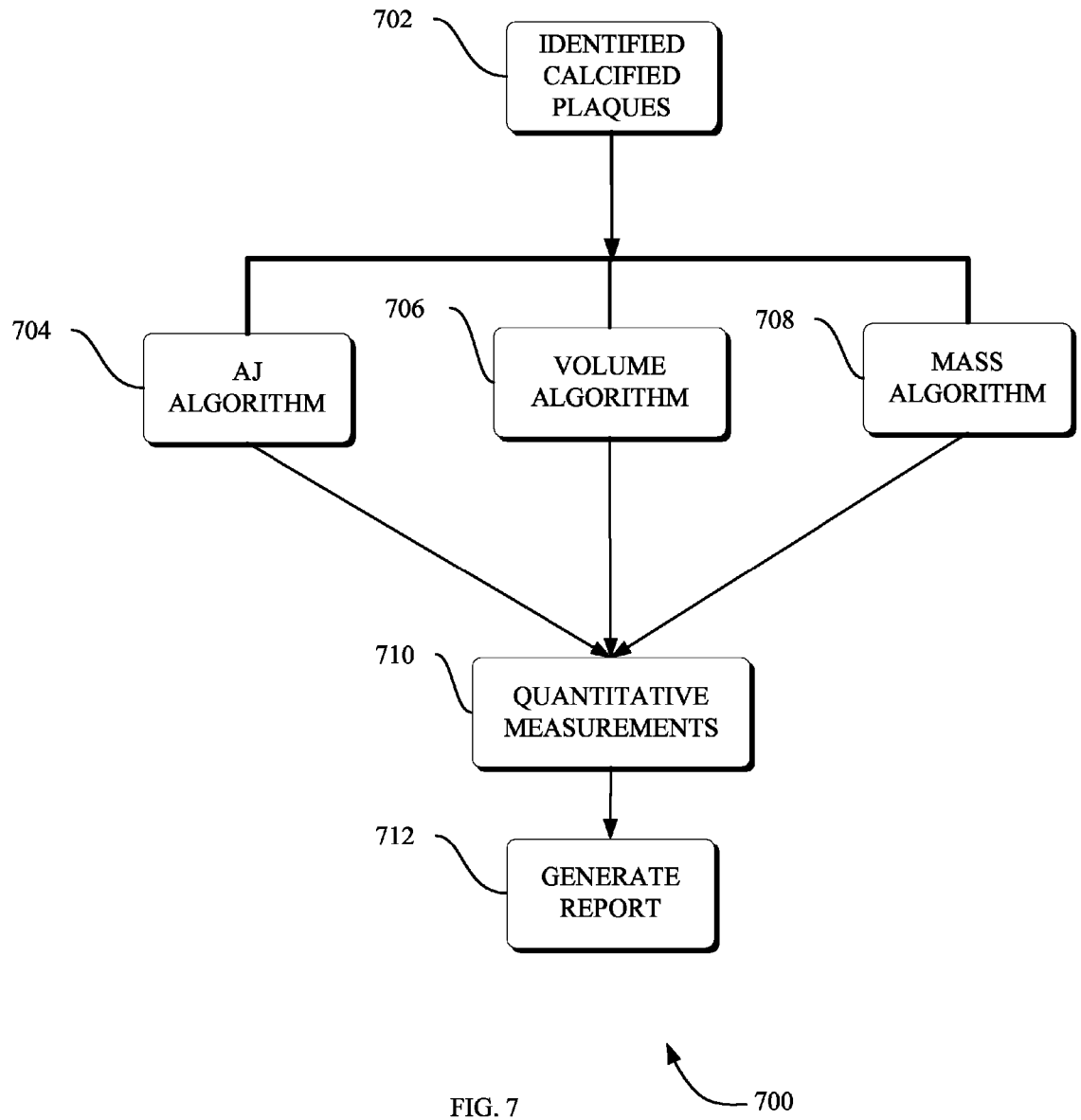
FIG. 7 is a flowchart of a method performed by a client according to an embodiment for generating a report of identified calcified plaques and their quantitative measurements.

FIG. 7 is a flowchart of a method 700 performed by a client according to an embodiment. Method 700 solves the need in the art for accurate detection and labeling of coronary artery calcification using an automated method.

Method 700 takes identified calcified plaques from storage 124 or plaque identification in real-time, performs AJ calcium scoring 704, performs volume determination 706, performs mass determination 708, determines quantitative measurements 710, and generates a report 712. There are three scores associated with quantifying the calcium plaque into a total calcium score. The Agatston Janovitz (AJ) score is a popular score among radiologists assessing cardiac images and is widely used. However, it is also the most susceptible to noise. The second score, referred to as a volume score, is used by research radiologists and is more reproducible than the AJ score. However, it is also limited in accuracy by the limitations on slice thickness and voxel dimensions. The third score, a mass score, is the most accurate of the three scores because it corrects for changes in slice thickness.

The Agatston Janovitz (AJ) algorithm 704 calculates calcium score. The Agatston Score or AJ Score includes the product of two numbers, a weighting factor derived from the peak intensity observed in a lesion and the area of the lesion in each slice it occupies, computed from the number of voxels that are above a given Hounsefield Units (HU) threshold and are connected together in-plane and if desired, across slices. A more complete description of the Agatston Score and analysis of CT images are described in Agatston A. S. et al, "Quantification of Coronary Artery Calcium Using Ultrafast Computed Tomography," J. Am. Coll. Cardiology 1990; 15:827-832, the complete disclosure of which hereby incorporated by reference in its entirety.

The volume algorithm 706 calculates the volume of the identified plaque. The volume of a calcified voxel is determined by multiplying the pixel area of a calcified voxel by the slice thickness. In determining the size or geometry of the fragments the volume of the voxels neighboring one another and satisfying the X-ray attenuation criterion is calculated. Further, a group of voxels having a total volume greater than or equal to a predetermined volume is interpreted as corresponding to a fragment. The image reconstructor 118 and master controller 120 calculate calcium score from the volume of the fragment.

The mass algorithm determines the mass of an identified plaque by calculating the average intensity of the voxels in the fragment multiplied by the volume of the fragment. For a background on attenuation, volume, and mass see the publication of Rumberger et al., which hereby incorporated by reference in its entirety, entitled "A rosetta stone for coronary calcium risk stratification: Agatston, volume, and mass scores in 11,490 individuals" and published in AJR Am. J. Roentgenol, 181:743-748) (2003).

In action 710 quantitative measurements are determined. The quantitative measurements are the calcium score, the volume, and the mass values that were obtained from the AJ algorithm 704, the volume algorithm 706, and the mass algorithm 708. These values are stored for each identified plaque and for each region of interest (ROI). Assuming, the crosshair tool 600 there would be a set of identified plaques for each quadrant. The identified plaques would then be summed for each region (quadrant) and the 3D bounding volume. Once the quantitative measurements are determined control passes to action 712 for further processing.

In action 712 a report listing the quantitative measurements of action 710 are combined into a report. The report aids in the diagnostic scorecard and provides a quick visual indication of calcium location in the regions identified by the crosshair tool 600.

Figure 8:
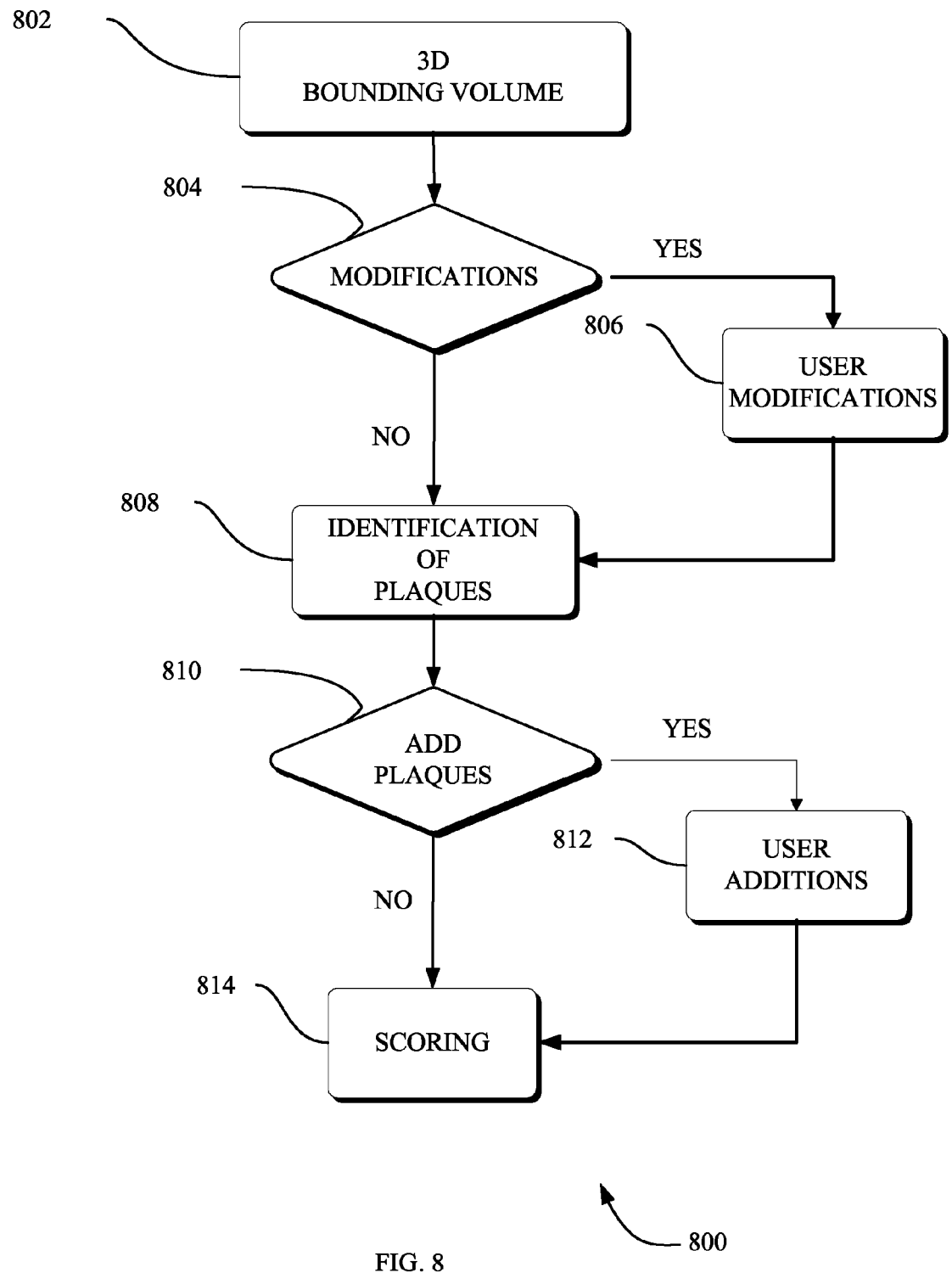
FIG. 8 is a flowchart of a method performed by a client according to an embodiment for allowing user interaction.

FIG. 8 is a flowchart of a method 900 performed by a client according to an embodiment. Method 800 solves the need in the art for accurate detection and labeling of coronary artery calcification using an automated method.

Method 800 allows for modifications to be made to the 3D bounding volume and identification of plaques. As shown when the 3D bounding volume is created 802 the software running on master controller 120 provides for modifications 804. When a user makes modifications 806 to the 3D bounding volume 802 they are incorporated or employed in the identification of plaques 808. The user is permitted 810 to add plaques 812 to already identified plaques 808. The identified plaques 808 and the added plaques 812 are then subjected to the determination of calcium scoring, determination of volume, and determination of mass as outlined with reference to method 700.

In some embodiments, methods 200-900 are implemented as a computer data signal embodied in a carrier wave, that represents a sequence of instructions which, when executed by a processor, such as processor 120 in FIG. 1, cause the processor to perform the respective method. In other embodiments, methods 200-900 are implemented as a computer-accessible medium having executable instructions capable of directing a processor, such as processor 120 in FIG. 1, to perform the respective method. In varying embodiments, the medium is a magnetic medium, an electronic medium, or an optical medium.

Apparatus 100 components of the image reconstruction 118, storage 124, and input/output device 122 can be embodied as computer hardware circuitry or as a computer-readable program, or a combination of both. In another embodiment, system 100 is implemented in an application service provider (ASP) system.

More specifically, in the computer-readable program embodiment, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or inter-process communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer 120 in FIG. 1, or on at least as many computers as there are components.

CONCLUSION

Automatic coronary artery calcium detection and labeling system is described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in procedural terms, one of ordinary skill in the art will appreciate that implementations can be made in an object-oriented design environment or any other design environment that provides the required relationships.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

We claim:

1. An automated method for detecting coronary artery calcification, the automated method comprising:
creating, using a processor, a three dimensional (3D) bounding volume by analyzing a set of images, wherein the bounding volume includes a heart;
applying a reticle on the created bounding volume so as to divide the bounding volume into regions;
analyzing each region to identify calcified plaques that exceed a predetermined value;
labeling each identified calcified plaque;
automatically determining a location of each labeled calcified plaque using the reticle; and
generating quantitative measurements for the identified calcified plaques that exceed a predetermined value.

2. The automated method of claim 1, wherein the quantitative measurements are one of calcium score, volume, mass.

3. The automated method of claim 1, wherein the set of images further comprises:
one or more image acquired using at least one of a computed tomography (CT) system, a magnetic resonance imaging (MRI) system, a positron emission tomography (PET) system, or a photon emission computed tomography (SPECT) system.

4. The automated method of claim 1, wherein creating a bounding volume further comprises:
segmenting the heart from the set of images by applying one or more model based segmentation approach, and lung segmentation and localization of the heart.

5. The automated method of claim 1, wherein analyzing each region to identify calcified plaques further comprises:
performing one or more thresholding, morphology, and centroid analysis.

6. The automated method of claim 1, the method further comprising:
proving a user interface (UI) for user initiated modification of the bounding volume, or identification of calcified plaques.

7. The automated method of claim 1, wherein the reticle creates at least one or more right coronary artery (RCA) region, left anterior descending artery (LAD) region, or left circumflex artery (LCX) region.

8. The automated method of claim 1, wherein generating quantitative measurements further comprises:
selecting one or more Agatston Janovitz (AJ) algorithm, volume algorithm, mass algorithm, or user-defined algorithm for calculating quantitative measurements.

9. The automated method of claim 7, the automated method further comprising:
generating a report showing the quantitative measurements for each region of the bounding volume as performed by the selected one or more algorithms for calculating quantitative measurements.

10. A non-transitory computer readable medium to detect coronary artery calcification, the having executable instructions stored thereon directing a processor to perform:
creating a three dimensional (3D) bounding volume by analyzing a set of images, wherein the bounding volume includes a heart;
applying a reticle on the created bounding volume so as to divide the bounding volume into regions;
analyzing each region to identify calcified plaques that exceed a predetermined value;
labeling each identified calcified plaque;
automatically determining a location of each labeled calcified plaque using the reticle; and
generating quantitative measurements for the identified calcified plaques that exceed a predetermined value.

11. The computer-accessible medium of claim 10, wherein the quantitative measurements are one of calcium score, volume, mass.

12. The computer-accessible medium of claim 10, the processor further performing: receiving user initiated modification of the bounding volume, or identification of calcified plaques.

13. The computer-accessible medium of claim 10, wherein the set of images further comprises:
one or more image acquired using at least one of a computed tomography (CT) system, a magnetic resonance imaging (MRI) system, a positron emission tomography (PET) system, or a photon emission computed tomography (SPECT) system.

14. The computer-accessible medium of claim 10, wherein creating a bounding volume further comprises:
segmenting the heart from the set of images by applying one or more model based segmentation approach, and lung segmentation and localization of the heart.

15. The computer-accessible medium of claim 10, wherein analyzing each region to identify calcified plaques further comprises:
performing one or more thresholding, morphology, and centroid analysis.

16. The computer-accessible medium of claim 10, wherein the reticle creates at least one or more right coronary artery (RCA) region, left anterior descending artery (LAD) region, or left circumflex artery (LCX) region.

17. The computer-accessible medium of claim 10, wherein generating quantitative measurements further comprises:
selecting one or more Agatston Janovitz (AJ) algorithm, volume algorithm, mass algorithm, or user defined algorithm for calculating quantitative measurements.

18. The computer-accessible medium of claim 15, the processor further performing:
generating a report showing the quantitative measurements for each region of the bounding volume as performed by the selected one or more algorithms for calculating quantitative measurements.

19. A system for detecting coronary artery calcification comprising:
a processor;
a storage device coupled to the processor; and,
software means operative on the processor for:
creating a three dimensional (3D) bounding volume by analyzing a set of images, wherein the bounding volume includes a heart;
applying a reticle on the created bounding volume so as to divide the bounding volume into regions;
analyzing each region to identify calcified plaques that exceed a predetermined value;
labeling each identified calcified plaque;
automatically determining a location of each labeled calcified plaque using the reticle; and
generating quantitative measurements for the identified calcified plaques that exceed a predetermined value;
wherein the reticle creates at least one or more right coronary artery (RCA) region, left anterior descending artery (LAD) region, or left circumflex artery (LCX) region.

20. The system of claim 19, wherein the set of images are one or more image acquired using at least one of a computed tomography (CT) system, a magnetic resonance imaging (MRI) system, a positron emission tomography (PET) system, or a photon emission computed tomography (SPECT) system;
- wherein creating a bounding volume is segmenting the heart from the set of images by applying one or more model based segmentation approach, and lung segmentation and localization of the heart;
- wherein analyzing each region to identify calcified plaques is performing one or more thresholding, morphology, and centroid analysis;
- wherein the quantitative measurements are one of calcium score, volume, mass.

21. The system of claim 19, the system further comprising:
- user interface (UI) for making user initiated modification of the bounding volume, or identification of calcified plaques.

22. The system of claim 19, wherein generating quantitative measurements further comprises:
- selecting one or more Agatston Janovitz (AJ) algorithm, volume algorithm, mass algorithm, or user defined algorithm for calculating quantitative measurements;
- generating a report showing the quantitative measurements for each region of the bounding volume as performed by the selected one or more algorithms for calculating quantitative measurements.

* * * * *